United States Patent [19]

Talonn

[11] Patent Number: 4,857,056
[45] Date of Patent: Aug. 15, 1989

[54] AUTO-FLUSH SYRINGE PUMP

[75] Inventor: Daniel A. Talonn, University City, Mo.

[73] Assignee: Sherwood Medical Company, St. Louis, Mo.

[21] Appl. No.: 215,649

[22] Filed: Jul. 6, 1988

[51] Int. Cl.⁴ .............................................. A61M 5/00
[52] U.S. Cl. ..................................... 604/135; 604/191; 604/82
[58] Field of Search .................. 604/82, 83, 191, 258, 604/135, 134, 131

[56] References Cited

U.S. PATENT DOCUMENTS

| | | | |
|---|---|---|---|
| 4,044,757 | 8/1977 | McWhorter et al. | 604/82 |
| 4,109,653 | 8/1978 | Kozam et al. | 604/191 |
| 4,563,175 | 1/1986 | Lafond | 604/191 |
| 4,689,042 | 8/1987 | Sarnoff et al. | 604/136 |

Primary Examiner—Stephen C. Pellegrino
Attorney, Agent, or Firm—Stanley N. Garber; Andrew J. Beck; Richard D. Allison

[57] ABSTRACT

A device for automatically administering predetermined amounts of medication from a syringe through a conduit to a patient is described. This device includes an automatic flushing mechanism which flushes the medication from the conduit after the completion of the medication dosage using a flush syringe containing a flush solution. A force derived from a spring is used to expel the medication and the flush solution from their respective syringes. Thus, the patient is insured a full dosage of prescribed medication without the need of continuous attention by hospital staff.

14 Claims, 2 Drawing Sheets

AUTO-FLUSH SYRINGE PUMP

FIELD OF THE INVENTION

This invention relates to a medical device useful for the intravenous line infusion of medication to a patient and more particularly to a device which not only permits the automatic infusion of said medication but imparts the capability of automatically flushing the line after infusion.

DESCRIPTION OF THE PRIOR ART

Modern medical facilities impart care to many patients, some over a considerable length of time. Many of these patients require medication and pain supplements during their stay and many of these prescriptions are applied intravenously. There continues to be a pressing need to reduce the time that the medical staff (i.e. doctors and nurses, for example) must spend with each patient in order to give more care to more and more patients. None the less, each patient requires the best of individual care. In the case where medication must be supplied to the patient, and especially in the case where the medication is supplied intravenously in intermittent doses (typical of antibiotic therapy) and over some length of time, medical care can be time consuming. The prior art has solved part of this problem by providing intravenous devices (both mechanical and electronic) which automatically dispense the required medication without the need for personal attention by the medical staff. These devices thus provide a constant, but controlled, pressure on the infusion device insuring that the required medication is dispensed in the manner prescribed. Thus, the care for the patient is provided by these devices with little or no attention by the hospital staff. However, there are some drawbacks to the automatic infusion devices of the prior art. One of the most serious is that after the automatic infuser of the prior art has completed the dose cycle, there remains in the lines leading to the patient some of the medication. The hospital staff must, therefore, return at the required time and manually flush out the lines leading to the patient to insure that the dosage is complete.

There exists a possible hazard to either the equipment or the patient should the medication remain stagnant (un-flushed) for long periods of time. Certain medications when used in high concentrations can inflame the veins of the patient at the point of medicinal entry when contact with the veins is prolonged. Furthermore, high concentrations of medication can also corrode or otherwise damage the lines to the patient if left stagnant for long periods of time. For at least these reasons, such medication should not remain stagnant in the lines for any great length of time.

Stagnant medication within the I.V. cannula can also result in blood clot formation. This is an undesirable condition. The hospital staff is extremely busy and knowing exactly when the cycle has been completed is difficult. There have been prior art elements which describe the use of devices to purge or flush lines after intravenous medication has been applied. These devices are, however, not automatic in nature and require that hospital staff return after the completion of medication to start the flush or purge thereof.

To minimize medication errors hospital pharmacies follow current medical practice by providing pre-filled I.V. medication into syringes. It would therefore, be convenient to utilize the pre-filled syringe directly with an automatic administering device.

Finally, most of the prior art elements designed to apply medication in automatic fashion are complicated and costly to prepare and use. Thus, since medical costs are already extremely high, there is a pressing need to utilize devices which are cost efficient.

It is an object of this invention to provide a means for automatically infusing intravenous medication to a patient and to provide a means for automatically flushing this device after the infusing has been completed to insure complete delivery of the medication.

It is also an object of this invention to provide such a means which is simple to use and reduces hospital costs efficiently.

SUMMARY OF THE INVENTION

These objects, among others, are achieved by providing a device for automatically administering predetermined amounts of fluids through a conduit to a patient, comprising a first syringe holding medication and a second syringe holding a flush solution each of said syringes including a barrel for containing fluid, a dispensing end and a plunger for exerting pressure within said barrel to expel said fluid through said dispensing end, said conduit jointly attached to both syringes through said dispensing ends, means for providing a force on said plunger of said medication syringe to dispense said medication through said conduit to said patient, means for transferring said force from said plunger of said medication syringe to said plunger of said flush syringe for expelling said flush solution into said conduit thereby insuring complete delivery of said medication to the patient, said transferring means responsive to the completion of the predetermined amount of said medication.

DETAILS OF THE INVENTION

Figure 1:
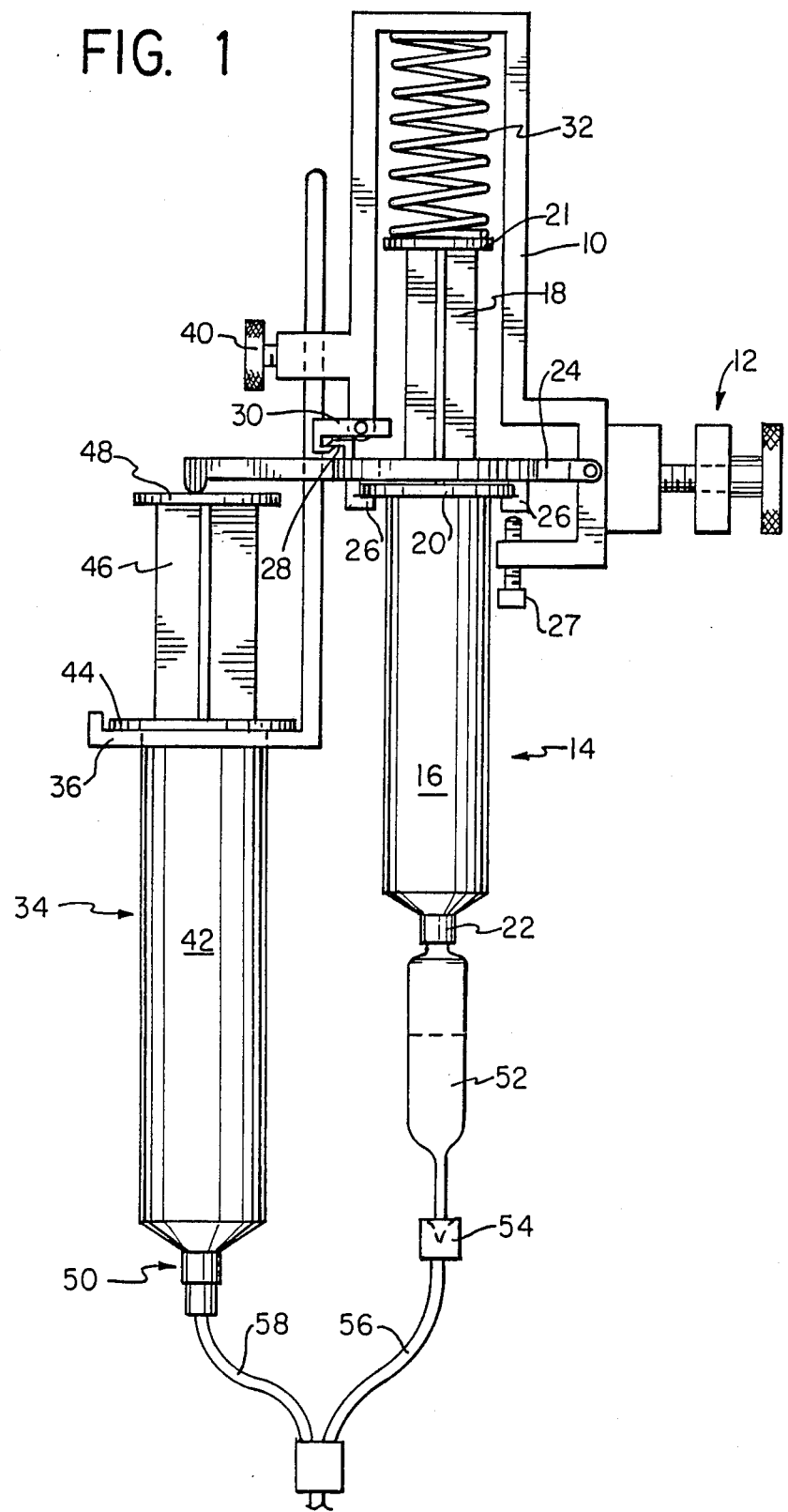
FIG. 1 shows a preferred embodiment of the present invention with two infusion syringes in a parallel arrangement and having a mechanical means for determining when one syringe dosage is complete and when the other should begin.

Referring to FIG. 1, there is shown a frame 10 which can be mounted to a typical intravenous pole commonly found in a hospital environment using clamp 12. A medication syringe 14 is preferably the type which includes a barrel 16 which houses medication to be administered to a patient, a plunger 18 slidably positioned therein, and a dispensing end 22 (such as a luer connector or a needle). The barrel 16 comprises a support flange 20 located around its upper portion. The plunger 18 comprises an upper flange 21 and a piston (not shown) attached to a lower portion of the plunger 18 within barrel 16 for causing medication to be dispensed through the dispensing end 22 when the plunger is depressed.

The medication syringe is secured to a mounting bar 24. Mounting tabs 26 are provided on mounting bar 24 and are positioned such that the support flange 20 of the barrel 16 slidably fits in between the mounting bar 24 and the mounting tabs 26, thereby, preventing vertical movement of the barrel 16 with respect to the mounting bar 24.

One end of the mounting bar 24 is pivotally attached to the frame 10. The mounting bar 24, during the dispensing of the medicine from the medication syringe 14, is held in a substantially horizontal position by a locking tab 28, located on the mounting bar 24 and a corresponding release tab 30, hingably fixed to the frame 10. The release tab 30 is positioned such that a portion overlaps the downward path of the upper flange 21 of the plunger 18. When released from the horizontal position, the mounting bar 24 swings downwardly around the pivot point. A flush limiter 27 is adjustably fixed to the frame 10 and limits the downward travel of the mounting bar 24.

A spring 32, held in a vertical position by the frame 10 is positioned such that when the medication syringe is inserted into the appropriate mounting tabs 26 of mounting bar 24, the spring 32 will become compressed against the frame 10 owing to the plunger 18 extending from the barrel 16. The compressed spring 32 will provide the necessary downward force for both the medication syringe 14 and the flush syringe as described below.

Alternatively, the spring 32 can be replaced by similar sources of force such as a compressed gas arrangement, a weight working under the influence of gravity, or an electric motor turning a screw.

A flush syringe 34 is located substantially parallel and adjacent to the medication syringe 14. The flush syringe 34 is constructed similarly to the medication syringe 14 and includes a barrel 42, a support flange 44 located around an upper portion of the barrel 42, a plunger 46 comprising an upper flange 48 and a piston (not shown), and a dispensing end 50. The flush syringe 34 holds a flush solution which "flushes" the I.V. line connected to the patient. By flushing the I.V. line, all the prescribed amount of medication enters the patient avoiding miscalculations due to medication remaining in the line or adverse effects due to cessation of flow. The line becomes free of the medication so that it can remain in place until a second medication dose is administered to the patient at a later time. The flush solution is usually a saline solution but may contain small amounts of other material to insure that harmful reactions do not occur. For example, heparin may be included to prevent clotting of the blood at the cannula site in the vein of the patient. The flush solution syringe can provide a single or multiple doses capable of providing several flushes.

A support bracket 36 accepts the support flange 44 and holds the flush syringe 34, preventing its downward movement with respect to the support bracket 36. The support bracket 36 is adjustably attached to the frame 10 by a locking knob 40, providing vertical positioning of both the support bracket 36 and the flush syringe 34 with respect to the frame 10.

The end of the mounting bar 24 which is not pivotally attached to the frame 10, extends over the upper flange 48 of the plunger of the flush syringe 34. This extension of the mounting bar 24 is such that the mounting bar 24, when released, will transmit the downward force of the spring 32 which is positioned over the medication syringe 14 to the plunger 46 of the flush syringe 34.

The dispensing end 22 of the medication syringe 14 is preferably in the form of a standard luer connector connected directly to a conventional I.V. administration assembly. The dispensing end 22 is attached to a drip chamber 52 (which can be of conventional design) which allows an operator to easily observe the flow rate of the medication dispensed. The output of this drip chamber 52 is attached to a one-way check valve 54, preferably connected directly or by way of a short length of single lumen I.V. line 56. The one way valve 54 is preferably incorporated into a "Y" intersection 55 and allows the flow of medication towards the patient only, preventing the reverse flow towards the medication syringe 14.

A length of single lumen main I.V. line 57 continues from the output of the "Y" intersection 55 and provides a path for either the medication of the medication syringe 14 or flush solution from the flush syringe 34 to follow to an intravenously positioned canula (not shown) on the patient. The dispensing end 50 of the flush syringe 34 is attached to the remaining input of the "Y" intersection 55, preferably connected directly or using a short length of I.V. line 58. This length of I.V. line 58 provides an entrance for the flush solution into the main line 57. The check valve 54 is positioned so that no flush solution can enter the I.V. line 56 and travel into the drip chamber 52.

In operation, the frame 10 is firmly attached to a conventional intravenous support using clamp 12. A predetermined amount of medication is drawn into the medication syringe 14 and a predetermined amount of flush solution is drawn into the flush syringe 34. The dispensing ends 50 and 22, of the flush syringe 34 and the medication syringe 14 are connected to the short I.V. line 58 and the drip chamber 52, respectively. The flush syringe 34 is first positioned onto the support bracket 36. The height of the support bracket 36 with respect to the frame 10 is adjusted such that the upper flange 48 of the extended plunger 46 of the flush syringe 34 lies just below the mounting bar 24 when the mounting bar 24 is locked in the horizontal position using release tab 30 and locking tab 28. The release tab 30 will preferably be pivotally attached to the frame 10 such that it will default, under its weight to a locking position with respect to the corresponding locking tab 28 and must be forced to an unlocked position. The flush limiter 27 is adjusted so that only a predetermined amount of flush solution will be administered.

The medication syringe 14 is positioned onto the frame 10 using the support flange 20 and the mounting tabs 26. The plunger 18, which is extending from the barrel 16, compresses the spring 32. The compressed spring 32 forces the plunger 18 further into barrel 16 and the medication out of barrel 16 and into the drip chamber 52. The medication is then regulated with a conventional roller clamp (not shown) past the check valve 54 and into the I.V. line 57 to the patient. This continues until all of the prescribed medication has been forced out of barrel 16, at which point the upper flange 21 of the medication syringe 14 hits the extended portion of the release tab 30 and releases mounting bar 24 from its horizontal position. The remaining force of the compressed spring 32 is now directed to the plunger 46 of the flush syringe 34 through the mounting bar 24. The flush solution is forced through the short line 58 and effectively flushes any residual medication remaining in the longer I.V. line 57 into the patient. The check valve 54 prevents the flush solution from entering the drip chamber 52.

When flushing is complete, the system can be left unattended until it is time to replace the empty medication syringe with a new one containing additional medication. The flush syringe 34 will not necessarily need replacing because only a portion of the full flush syringe 34 is required to flush the length of I.V. line 57 typically used. However, it is necessary to re-adjust the height of the support bracket 36 to account for the lower position of the plunger 46 owing to the loss of flushing solution. The adjustment should leave the locked mounting bracket 24 lying just above the upper flange 48 of the flush syringe 34.

Figure 2:
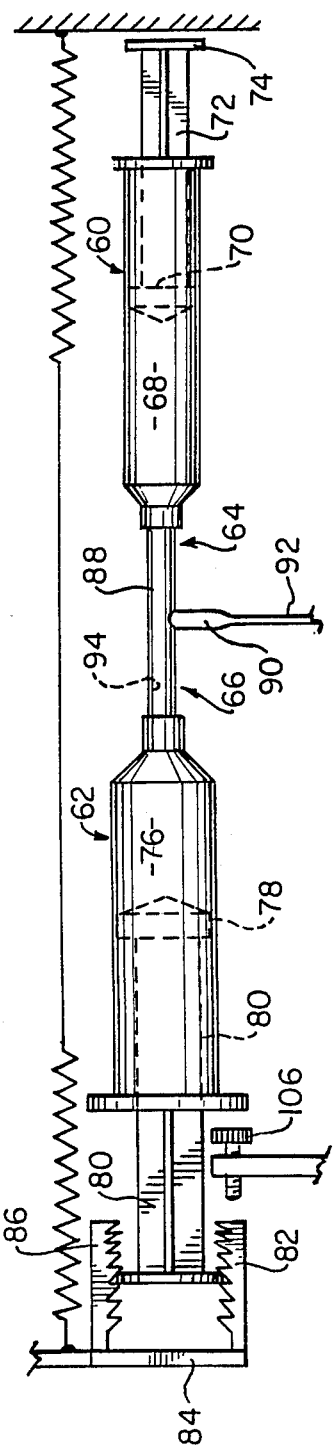
FIG. 2 shows another embodiment wherein the two syringes are linearly opposed and having a differential pressure means for determining when one syringe dosage is complete and when the other should begin.

FIG. 2 shows an alternative embodiment in which fluid pressure of the medicinal solution controls the timing of the flush. A medication syringe 60 and a flush syringe 62 are positioned in an opposing arrangement with their respective dispensing ends 64 and 66 facing one another. The medication syringe 60 can be conventionally constructed having a barrel 68, a plunger 72 comprising a piston 70 and an upper flange 74. The flush syringe 62 can also be conventionally constructed having a barrel 76, a plunger 80 comprising a piston 78 and an upper flange 82. With the present invention, the flush syringe 62 must be larger than the medication syringe 60, making it usable for delivery of multiple flush doses. The surface area of the piston of the flush syringe 62 is larger than the surface area of the piston 70 of the medication syringe 60. Therefore, when equal force is applied to both plungers 72 and 80 of the medication syringe 60 and the flush syringe 62, respectively, the pressure of the medicinal fluid forced through the dispensing end 64 from the medication barrel 68 by the smaller piston 70 will be greater than the pressure of the flush solution forced through dispensing end 66 from the flush barrel 76 by the larger piston 78.

The two barrels 68 and 76 of the two syringes 60 and 62, respectively, are held stationary with respect to each other by a conventional means such as clamping the barrels to a surface or frame (not shown) or any other effective method.

A clip 84 is positioned around the upper flange 82 of the flush syringe 62. This clip 84 is shaped such that it can be clipped onto and removed from the upper flange 82 of the flush syringe 62 quickly and easily. A "C" shaped clip 84 is contemplated, defining a vertical wall and two horizontal walls. The "C" shaped clip 84 can be slid onto and removed from the upper flange 82 by pushing it sideways with respect to the upper flange 82.

Ratchet teeth 86 are preferably positioned along the two inside horizontal walls of the clip 84 which engage the edge of the upper flange 82. The ratchet teeth 86 are shaped such that linear movement of the handle flange 82 towards the vertical wall of the clip 84 is prevented. A flush limiting adjustment screw 106 is fixed to the frame (not shown) which holds the two syringes in place and limits the amount of flush delivered through an I.V. line to the patient by contacting either a contact point of the ratchet clip or the handle flange. The ratchet teeth 86 will permit incremental linear movement of the upper flange 82 away from the vertical wall of the clip 84. The magnitude of the incremental movement corresponds to the spacing of the ratchet teeth 86, the larger the ratchet spacing, the greater the distance moved by the upper flange 82 before locking into the next adjacent ratchet teeth 86 and the greater the distance defined between the limiting screw 106 and the ratchet clip and therefore the further the plunger will travel into the flush syringe before being stopped by the limiting screw 106. The distance between the contact surface of the limiting screw 106 and the ratchet clip contact point is an indication of the amount of the next administered dose. The quantity of solution used for each flushing is first set by adjusting the limiting screw 106 with respect to one of the ratchet teeth. After each flush, the clip 84 is then readjusted to effectively repeat the previously set flush solution dose for the administering of the next flush.

The ratchet teeth 86 can alternatively be substituted with a single slot or multiple slots for incremental adjustment, for receiving the upper flange 82 of the plunger of the flush syringe 62. The slots (not shown) are positioned along the clip 84 in a similar fashion to the ratchet teeth arrangement discussed above, the distance that each slot or multiple slots moves the contact point of the clip from the contact surface of the limiting screw 106 is an indication of the dose of each flush administered.

Figure 3:
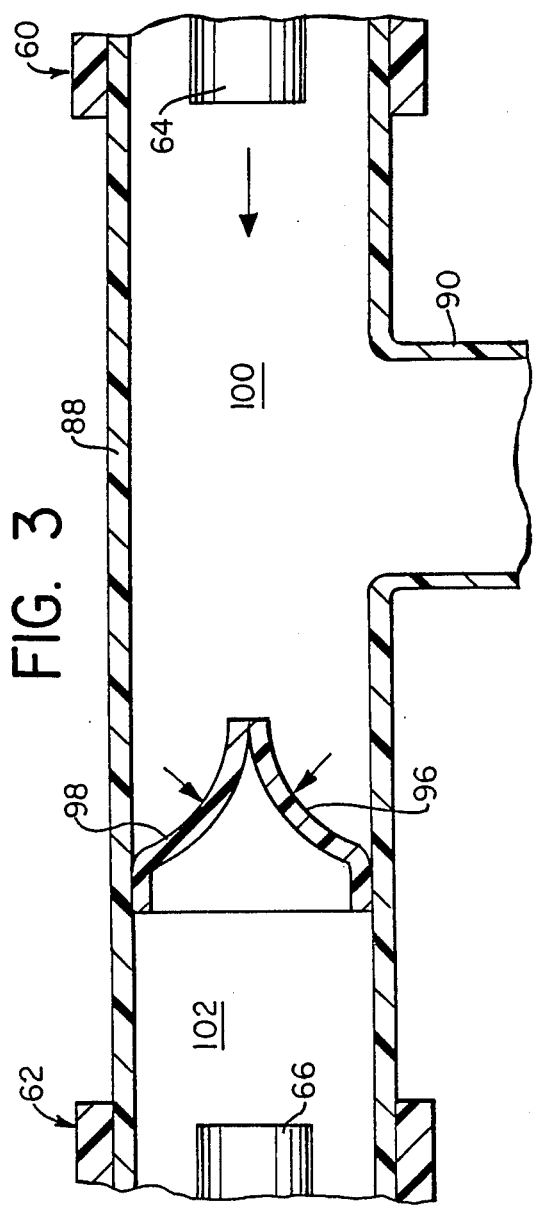
FIG. 3 shows the details of a preferred one way valve used with the embodiment shown in FIG. 2.

Both dispensing ends 66 and 64 of the flush syringe 62 and the medication syringe 60, respectively, are attached to the opposing ends of a valve tube 88. The diameter of the valve tube 88 is less than the diameter of either syringe barrel 60 or 62. An exit tube 90 is connected to the valve tube 88 preferably, but not required, in the center of the valve tube 88, thereby, creating a "T" connector which connects the two dispensing ends 64 and 66. An I.V. line 92 is connected to the other end of the exit tube 90 and carries the dispensing fluids from the valve tube 88 to a patient (not shown). A one-way valve 94 is located within the valve tube 88 between the flush dispensing end 66 and the exit tube 90. The valve 94, which is kept closed by the higher pressure of the medication fluid during administering of the medication, prevents the medication which is expelled at a higher pressure from forcing its way into the flush syringe 62 and not to the patient. The valve 94 will be opened, allowing flush solution from the dispensing end 66 to flow through the one-way valve 94 to the exit tube 90, only when the pressure of the medicinal fluid within the valve tube 88 from the dispensing end 64 is less than the pressure of the flush solution from the flush syringe 62. This will occur when the piston 70 of the medication syringe has reached the end of its travel thereby forcing no more medication through the dispensing end 64. The construction of the valve 94 can be two flexible flaps 96 and 98 as shown in FIG. 3 which are fitted together so that a portion of each face along an edge is in contact and that a sideways "V" shape is created. Fluid pressure on the medication side 100 of the flap valve in FIG. 3 must be less than the fluid pressure on the flush side 102 of the same valve in order for the flush solution from the flush side 102 to travel through the flap valve to side 100. A ball-and-spring type valve could also be used in place of the one-way flap valve 94, as well as other conventional one-way valves.

A spring 104 extends the length of the two opposing syringes 60 and 62 with fully extended plungers 72 and 80, respectively. The spring 104 is attached to both the upper flange 74 of the medication syringe 60, either directly or through a bracket (not shown), and the ratchet clip 84 which is positioned around the upper flange 82 of the flush syringe 62. This spring 104 exerts an equal compressive force on the two plungers 72 and 80 of the medication syringe 60 and the flush syringe 62, respectively. Other spring arrangements and other sources of force can be used as long as an equal compressive force is provided for both plungers 72 and 80.

The limiting screw 106 will prevent further movement of the piston 78 into the barrel 76 of flush syringe 62 by making contact with either a portion of the ratchet clip 84 or the upper flange 82.

In operation, the medication syringe 60 is prepared with the appropriate medication which is to be administered to the patient, and the flush syringe 62 is refilled, if necessary, with the appropriate flush solution. The outlets 64 and 66 of the medication syringe 60 and the flush syringe 62 are then connected to the appropriate inlets of valve tube 88 and both syringes are attached to the frame (not shown). The spring 104 which is attached to the ratchet clip 84 and the bracket (not shown) is positioned such that the bracket snugly butt against the upper flange 74 of the medication syringe 60. The ratchet clip 84 is slid sideways onto the upper flange 82 of the flush syringe 62. The limiting screw 106 has been adjusted so that it rests against the surface of the ratchet clip 84 thereby temporarily preventing inward movement of the plunger 80 into the barrel 76 of the flush syringe 62. The bracket is movable with the linear movement of the plunger 72 of the medication syringe 60 and can be temporarily secured by any conventional means such as a set screw or a second bracket selectively secured to the frame or any other means to prevent the dispensing of medication until the user is ready. The flow of medication can also be prevented using a conventional tube clamp on the I.V. line (not shown).

When ready, the limiting screw 106 is adjusted an appropriate predetermined distance from the ratchet clip 84. This distance is indicative of the amount of flush solution that will be dispensed into the I.V. lines. Alternatively, this distance could be adjusted by pulling the ratchet clip 84 away from the upper flange 82 of the flush syringe 62 an appropriate number of ratchet teeth 86. The securing bracket (if one is used) holding the medication plunger 72 is moved so that the compressive force from spring 104 pulls the two plungers of both syringes together. The pressure developed by the comparatively smaller cross-section medication piston 70 of the dispensing medication within the valve tube 88 will be greater than the pressure of the flush solution dispensed from the end 66 into the valve tube 88. The greater medication pressure will keep the one way valve 94 closed and will thereby prevent any flush solution from passing the valve 94 and preventing the flow of medication into the flush syringe. After the patient receives the predetermined dose of medication administered at a rate determined by a roller clamp or other I.V. flow regulator and the force of the spring 104, the medication piston 70 will stop with respect to the medication barrel allowing the fluid pressure in tube 88 to decrease. The remaining potential energy in the still expanded spring 104 will provide the flush solution dispensed from end 66 with the greater fluid pressure necessary to pass through the one way valve 94, into the valve tube 88 and to the patient through the I.V. line 92, thereby "flushing" the medication administering system. The flush solution to the patient will halt when the ratchet clip 84 makes contact with the limiting screw 106.

Owing to the amount of solution typically required to "flush" an I.V. line, the flush syringe 62 can remain secured to the frame and used for multiple flushes. When a new medication syringe is prepared and secured into the frame, the ratchet clip 84 need only be pulled further off the plunger 82 to re-set the predetermined quantity of flush solution to be later dispensed into the I.V. line 92.

By employing a multiplicity of these devices it would be possible to dispense a plurality of medications over a controlled period of time and thereafter flushing the I.V. line with a predetermined amount of solution automatically. Timers can be used to actuate the spring 104 to begin each medication. Thus, for a patient requiring both pain and healing medications, for example, there might be two of these devices with separated flush syringes in each or a modified device capable of holding two (or more) syringes having a different medication in each whereby the medications of each syringe flow to the patient using the same I.V. line and having a single flush syringe provided for flushing the single length of I.V. line when the last medication dispensing has been completed. Timers can also provide a convenient method of activating the force (spring 104) applied to the syringe plungers when the interval of time between medications is long and it is otherwise inconvenient to personally administer the medication. A bell, or an equivalent alarm can also be included so as to signal the hospital staff at the completion of the medication or the flush cycle.

What is claimed is:

1. A device for administering medication to a patient through a fluid conduit and thereafter automatically flushing said conduit with a flush solution, said device comprising;
    a first syringe having a first barrel for holding said medication, a first dispensing end, and a first plunger located within said first barrel for expelling said medication through said first dispensing end;
    a second syringe having a second barrel for holding said flush solution, a second dispensing end, and a second plunger for expelling said solution through said second dispensing end;
    means connecting said fluid conduit to said dispensing ends of both syringes and to said patient;
    means for providing a force to said first plunger for dispensing said medication from said first syringe into said fluid conduit; and
    means for transferring said force exerted on said first plunger to said second plunger for dispensing said flush solution from said second syringe into said conduit, said transferring means responsive to the completion of the dispensing of a predetermined amount of said medication from said first syringe.

2. A device for administering medication to a patient through a fluid conduit and thereafter automatically flushing said conduit with a flush solution, said device comprising;
    a first syringe having a first barrel for holding said medication, a first dispensing end, and a first plunger located within said first barrel for expelling said medication through said first dispensing end;
    a second syringe having a second barrel for holding said flush solution, a second dispensing end, and a second plunger for expelling said solution through said second dispensing end;
    a valve tube having a one way valve therein, and an exit tube attached thereto and attached to said fluid conduit, said valve tube positioned between said dispensing ends such that medication from said first syringe and solution from said second syringe is expelled into said valve tube on either side of said one way valve, said exit tube attached to said valve tube such that medication expelled from said first syringe flows directly into said exit tube and through said fluid conduit to said patient, said one way valve positioned between said exit tube and said dispensing end of said second syringe such that solution expelled from said second syringe must pass through said one way valve before reaching said exit tube, said valve operative to completion of medication administering;

means connecting said fluid conduit to said dispensing ends of both syringes to said valve tube; and means for providing a force to both plungers for dispensing their respective fluids into said valve tube.

3. The device according to claim 2 wherein said first plunger of said first syringe has a smaller surface area than said second plunger of said second syringe such that said force exerted on said first plunger expels said medication through said first dispensing end with greater pressure than said solution expelled through said second dispensing end by said second plunger from said force.

4. The device according to claim 3 wherein said medication having greater pressure dispensed into said valve tube from said first dispensing end prevents said one way valve from opening thereby preventing said medication from entering said second syringe having less pressure, and preventing said flush solution from passing through said one way valve and into said exit tube, said medication having greater pressure than said solution until a predetermined amount of medication is dispensed, at which point the pressure of said solution will be greater and said one way valve will open, allowing said solution to reach said exit tube.

5. The device according to claim 1 further comprising means to limit the amount of medication and solution dispensed.

6. The device according to claim 5 wherein said limiting means comprises a set screw which indirectly prevents said plungers of either syringe from further movement into their respective barrels.

7. The device according to claim 2 further comprising means for limiting the amount of medication and solution dispensed, a ratchet clip which fits around a connecting portion of either of said plungers and which is aligned to make contact with said limiting means, said ratchet clip having ratchet teeth disposed thereon such that said clip can be pulled from said connecting portion thereby separating said ratchet clip from said limiting means an incremental distance determined by said ratchet teeth, said distance determining the amount of medication or flush solution delivered to said fluid conduit.

8. A device for dispensing at least two fluids sequentially from at least two syringe-type containers, said device comprising;

a frame;

a mounting bar pivotally attached to said frame, said mounting bar selectively pivotal from a first position to a second position;

a first syringe containing a first fluid, attached to said mounting bar;

a second syringe containing a second fluid, attached to said frame;

means for forcing said first fluid from said first syringe; and a trigger responsive to the completion of the dispensing of a predetermined amount of said first fluid from said first syringe for allowing said mounting bar to move from said first position to said second position, said mounting bar thereafter transmitting said force to said second syringe such that said second fluid is forced from said second syringe.

9. The device according to claim 8 wherein said first fluid is a medication and said second fluid is a flush solution.

10. A device for administering a first fluid to a patient from a first syringe through a fluid conduit, and thereafter automatically administering a second fluid to the patient from a second syringe through said conduit, said device comprising:

a first syringe having a first barrel for holding a first fluid, a first dispensing end, and a first plunger located within said first barrel for expelling said first fluid through said first dispensing end;

a second syringe having a second barrel for holding a second fluid, a second dispensing end, and a second plunger for expelling said second fluid through said second dispensing end;

means connecting a fluid conduit to said dispensing ends of both syringes and to said patient;

means for moving said first plunger to dispense said first fluid from said first syringe into said fluid conduit;

means for moving said second plunger to dispense said second fluid from said second syringe into said fluid conduit; and means for initiating movement of said second plunger by said means for moving said second plunger responsive to the completion of a predetermined movement of said first plunger.

11. The device according to claim 10 wherein said means for initiating includes means for preventing movement of said second plunger during the predetermined movement of said first plunger, and means for permitting movement of said second plunger responsive to completion of said predetermined movement of said first plunger.

12. The device according to claim 11 wherein said means for permitting second plunger movement includes means to operatively connect said means for moving said first plunger to said second plunger, said connecting means responsive to the completion of said predetermined movement of said first plunger.

13. The device according to claim 11 wherein said means for preventing second plunger movement includes means for blocking said connection of said second dispensing end to said conduit during said predetermined movement of said first plunger and said means for permitting second plunger movement includes means for opening said connection of said second dispensing end to said conduit responsive to the completion of said predetermined movement of said first plunger.

14. A sequentially dispensing device for controlling the delivery of predetermined amounts of a first fluid and a second fluid from first and second inputs, respectively, to an output, the device comprising;

a first conduit connected at an input end to said first input for receiving said first fluid;

a second conduit connected at an input end to said second input for receiving said second fluid, output ends of said first and second conduit being connected to said output;

means connected to said inputs for providing said first fluid at a higher pressure at said first input within said first conduit and providing said second fluid at a lower pressure at said second input within said second conduit;

means for decreasing the pressure of said first fluid in said first conduit to less than the pressure of said second fluid in said second conduit; and a one way valve mounted in said second conduit for controlling the flow of said fluids from each of said inputs to said output, said second conduit responsive to relative fluid pressure of said first fluid at said first input and said second fluid at said second input, such that when the pressure at said first input is greater than the pressure at said second input, the valve is closed preventing flow through said second conduit and when the pressure at said second input is greater than the pressure at said first input, the valve is open, allowing fluid to flow through said second conduit.

* * * * *